US005834249A

United States Patent [19]
Furukawa et al.

[11] Patent Number: 5,834,249
[45] Date of Patent: Nov. 10, 1998

[54] PROCESS FOR PRODUCTION OF PROTEIN

[75] Inventors: Kazuaki Furukawa, Tatebayashi; Keijiro Sugimura, Ashikaga; Kazuhiro Ohsuye, Ohra-gun, all of Japan

[73] Assignee: Suntory Limited, Osaka, Japan

[21] Appl. No.: 759,945

[22] Filed: Dec. 3, 1996

Related U.S. Application Data

[63] Continuation of Ser. No. 303,191, Sep. 8, 1994, abandoned.

[30] Foreign Application Priority Data

Sep. 8, 1993 [JP] Japan ..................................... 5-257881

[51] Int. Cl.$^6$ .............................. C12P 21/02; C12N 5/06; C07K 14/54; C07K 14/57
[52] U.S. Cl. ...................... 435/70.5; 435/70.1; 435/70.3; 435/219; 435/354; 435/355; 435/357; 435/358; 435/360; 530/351
[58] Field of Search .................................. 435/70.1, 70.3, 435/70.5, 358, 360, 354, 355, 357, 219; 530/351

[56] References Cited

U.S. PATENT DOCUMENTS

| | | | |
|---|---|---|---|
| 4,216,203 | 8/1980 | Johnston | 424/85 |
| 4,218,478 | 8/1980 | Omura et al. | 424/324 |
| 4,690,918 | 9/1987 | Beppu et al. | 514/23 |
| 4,946,999 | 8/1990 | Koseki et al. | 562/452 |
| 5,324,640 | 6/1994 | Honjo et al. | 435/69.52 |

FOREIGN PATENT DOCUMENTS

| | | |
|---|---|---|
| B-56-46797 | 11/1981 | Japan . |
| 57-074 093 | 5/1982 | Japan . |
| A-57-74093 | 5/1982 | Japan . |
| 59-082 093 | 5/1984 | Japan . |
| B-60-18398 | 5/1985 | Japan . |
| A-63-185387 | 7/1988 | Japan . |
| A-1-104168 | 4/1989 | Japan . |
| 1-257 492 | 10/1989 | Japan . |
| A-1-257492 | 10/1989 | Japan . |
| A-2-190193 | 7/1990 | Japan . |
| B-47648 | 8/1992 | Japan . |
| B-5-32031 | 5/1993 | Japan . |
| A-6-313000 | 11/1994 | Japan . |

OTHER PUBLICATIONS

Feder et al, Scientific American 248(1):36–43 (1990).
The Merck Index (11th Ed, 1989) p. 1518.
Gibco/BRL Life Technologies Catalog, 1993 pp. 4.20 to 4.24.
M. Yoshida et al., "Potent and Specific Inhibition of Mammalian Histone Deacetylase Both in Vivo and in Vitro by Trichostatin A*", The Journal of Biological Chemistry, vol. 265, No. 28, pp. 17174 to 17179 (1990).
Taisha, "Analyses of Eukaryotic Cell Cycle Control Using Novel Inhibitors for $G_1$ and/or $G_2$", vol. 28, Supp., Gan 91, pp. 131–139 (1991) (partial translation).
Tanpakushitsu Kakusan Koso, "Regulation of Chromatin Structure and Its Transcriptional Activity by Histone Acetylation", vol. 37, No. 6, pp. 959–969 (1992) (partial translation).
K. Mizuno et al., "Peptide C–Terminal c–Amidating Enzyme Purified to Homogeneity from *Xenopus Laevis* Skin", Biochemical and Biophysical Research Communications, vol. 137, No. 3, pp. 984–991 (1986).
R. Fukunaga et al., "Constitutive Production of Human Interferons by Mouse Cells With Bovine Papillomavirus as a Vector", Proc. Natl. Acad. Sci. USA, vol. 81, pp. 5086–5090 (1984).
Yoshida et al., "Potent and Specific Inhibition of Mammalian Histone Deacetylase Both in Vivo and in Vitro by Trichostatin A", *Journal of Biological Chemistry*, (1990) 265(28):17174–17179.

*Primary Examiner*—Francisco C. Prats
*Attorney, Agent, or Firm*—Burns, Doane, Swecker & Mathis, L.L.P.

[57] ABSTRACT

A process for production of a desired protein comprising the steps of:
 a culturing animal cells capable of producing the desired protein in a medium containing trichostatin compounds; and
 recovering the desired protein from the culture.

20 Claims, No Drawings

PROCESS FOR PRODUCTION OF PROTEIN

This application is a continuation of application Ser. No. 08/303,191, filed Sep. 8, 1994 now abandoned.

BACKGROUND OF THE INVENTION

1. Field of the Invention

The present invention relates to a process for production of proteins. More particularly, the present invention relates a method for enhancing the productivity of proteins by adding a trichostatin to a culture medium.

2. Related Art

Various useful substances such as biologically active proteins are produced in an industrial scale, using as hosts microorganisms, animal cells, etc. by recombinant DNA technology.

Although the use of microorganisms such as E. coli for the production of useful substances such as proteins is advantageous in the productivity, they are not applicable in the case where a desired protein to be produced has a high molecular weight and a complicated tertiary structure, it is difficult to refold the protein formed by refolding by host from E. coli extracts, or where a desired protein to be produced must be modified by for example glycosylation for exhibition of its biological activity. To produce such a protein, animal cells are usually used. Known animal cells include CHO-K1 (Chinese hamster ovary cell; ATCC CCL61), CHO-K1-derived dihydrofolate reductase (DHFR)-lacking strain, C127I (mouse breast cancer cell; ATCC CRL 1619), BHK (new-born hamster kidney cell; ATCC CCL 10), Vero (African green monkey kidney cell; ATCC CCL-81) etc. However, in comparison of animal cells with microbial cells, the animal cells are disadvantageous in that their growth rate is low, culture media are expensive, and their productivity for a desired product is low. It is difficult to change low growth rate, because it relates to properties of the cells per se. In addition, basic improvement of cost of culture media is difficult because the media must contain all of essential components necessary for the growth of the cells. Accordingly, in an industrial production of a desired product using animal cells, an improvement of productivity, i.e., an increase of the desired product produced by each cell is important.

So far, for enhancement of productivity of a desired protein by animal cells, straight chain alkanoic acids such as butyric acid (Japanese Examined Patent Publication (Kokoku) No. 56-46797, and Japanese Unexamined Patent Publication (Kokai) No. 1-257492); glucocorticoids such as hydrocortisone, dexamethasone etc. (Japanese Examined Patent Publication (Kokoku) No. 5-32031, and Japanese Unexamined Patent Publication (Kokai) No. 57-74093); dimethylsulfoxide (DMSO; Japanese Examined Patent Publication (Kokoku) No. 60-18398); and the like have been used. It is reported that butyric acid exhibits an action to inhibit histone deacetylase resulting in high acetylation of histon, and an action to induce a differentiation in a certain cell. Since the acetylation of histone is suggested as one of phenomena relating to an expression of genes, it is speculated that the enhancement of productivity by butyric acid is caused by high acetylation of histone among various actions of butyric acid. However, this has not yet been confirmed because of diversity of actions of butyric acid. DMSO is known to have an action to the cell membrane, an action to include differentiation, and the like. Hydrocortisone, one of corticoids, is a substance having a variety of functions, such as, growth promotion or growth inhibition depending on the cell species, improvement of productivity of a desired product, etc. Effective concentrations of the above-mentioned substances to be added are different depending on the cell species, and are 0.1 to 10 mM for butyric acid, the order of $\mu$M for hydrocortisone, 0.05 to 2% (some mM to some hundreds mM) for DMSO.

As can be seen from the above, for an increase of productivity, the above-mentioned substances must be used at a high concentration which may cause cell-damage. If cells are damaged, not only a desired product may not be sufficiently produced due to decrease of viable cells, but also purification of the desired product may be hampered by cell components (i.e. impurities) released into a medium from the damaged cells. In addition, the desired product may be degraded by proteases contained in the cell components released to the medium. Accordingly, one cannot say that the substances so far used are suitable for enhancement of productivity of a desired substance by cell culture.

Accordingly, to enhance the productivity of a desired product using animal cells, an inducing substance which is effective at a low concentration and does not cause the cell-damage is sought.

SUMMARY OF THE INVENTION

Accordingly, the present invention provides a process for production of a desired protein comprising the culture steps for animal cells capable of producing said desired protein in a medium containing a trichostatin compound, and recovering the desired protein.

DETAILED DESCRIPTION OF THE INVENTION

Animal cells used in the present invention are any animal cells which can produce a desired protein. The animal cells include primary cells isolated from any animal, cultured cells, immortalized cells, and established cell lines. The animal cells used in the present invention include cells which intrinsically have an ability to produce a desired protein; cells which are induced to have an ability to produce a desired protein, for example, by stimulation with a cytokin such as an interferon, an interleukin etc.; genetically engineered cell into which a gene for a desired protein is introduced, for example hybridoma cells, cells transformed or transfected with, for example a recombinant gene such as an expression vector such as a plasmid, a viral vector etc.

The animal cells used in the present invention may be derived from any animal, including invertebrates and vertebrates. The invertebrates include insects such as silk worm, armymorm; and the invertebrates include mammals, fishes, birds, etc. The animal cells used in the present invention are preferably those derived from mammals such as small animals for example murines such as mouse or rat, guinea pig; middle or large animals such as cat, rabbit, pig, cattle, sheep, goat, etc.; and the primates, i.e., monkeys and human.

The particular cell lines useful in the present invention are, for example, CHO, COS, BHK, Vero, C127, Hela, Jurkat, Namalwa, Sf-9 etc.

The protein produced by the present process include any peptides or proteins, including peptide hormones or proteinaceous hormones such as insulin, growth hormones, calcitoniss (CT), parathyroid hormone (PTH), adenocorticotropic hormone (ACTH), thyroid stimulating hormone (TSH), prolactin, vasopressin; cytokines for example, interferons such as IFN-α, IFN-β, NFN-γ, and their derivatives; interleukins such as IL-1, IL-2, IL-3, IL-4~IL-12; enzymes such as furin, intestical enterokinase, PC1/PC3, PC2/PC4; blood coagulation factors such as tissue plasminogen activator (TPA), FVIII, FIXa, FXa; and other useful peptides and proteins such as erythropoietin (EPO), bone morphogenetic protein, etc.

According to the present inventions, any media in which animal cells can grow and produce a desired protein, including serum-free media and serum-containing media can be used. Typical busal media are, for example, MEM (minimum essential medium), DMEM (Dulbecco's modified eagle medium), BME (basal medium eagle), RPM1-1640, F-12, etc.

A medium used in the present process contains at least one trichostatin compound which induces high acetylation of histone and which does not exhibit cell damage or exhibits a reduced cell-damage action. The trichostatin compounds include trichostatin A (TSA), trichostatin B, and trichostatin C, as well as derivatives thereof having the above-mentioned properties.

The most preferably trichostatin compound is TSA. TSA is a substance which was first found as an antibiotic against a some range of fungi, and at present, is used as a cell growth inhibitor specific to the G1 and G2 phases in the cell cycle wherein the cell growth inhibition is caused by inhibition of histone deacetylase (The Journal of Biological Chemistry, Vol. 265, No. 28, p. 17174–17179, 1990; Taisha Vol. 28, extra number/Gan'91, p. 131–139, 1991; Tanpakushitsu Kakusan Koso, Vol. 37, No. 6, p. 959–969, 1992; Japanese Examined Patent Publication (Kokoku) No. 4-47648).

A concentration of a trichostatin compound such as TSA is between 10 nM and 500 nM, more preferably between 20 nM and 300 nM, and more preferably between 50 nM and 300 nM, and for example about 200 nM, in a culture medium.

The present inventors consider that TSA enhances a productivity of a desired protein by causing high acetylation of histone through an inhibition of histone deacetylase enzyme, although the present inventors are not aware of a report describing the use of TSA for production of a substance. The present inventors found that a trace of TSA added to a culture medium remarkably increases an amount of a desired protein in animal cell culture. Note that "high acetylation" of histone means that the $\epsilon$-amino of Lys residue in histon is acetylated.

First, to compare an effect of TSA and that of conventional substances so far used for enhancement for the production of a desired protein, i.e., DMSO, butyric acid and hydrocortisone, effects of the TSA, DMSO, butyric acid and hydrocortisone on $3\mu$-1S cells which are suspending CHO cells producing a peptidyl C-terminal $\alpha$-amidating enzyme (AE) (see Reference Example) were tested.

The $3\mu$-1S cells were inoculated into a 24-well culture plate (Corning) with a serum-free medium which was F-12 medium (Ajinomoto) supplemented with insulin and transferrin. Next, TSA, DMSO, butyric acid or hydrocortisone was added to a predetermined concentration, and culture was carried out. To use TSA, powdery TSA (Wako Pure Chemical) was dissolved in methanol or ethanol to prepare solution containing 1 mM TSA, which was then stored at −20° C. for use, the TSA solution was diluted with a basal medium (F-12, DMEM, RPMI 1640, etc.), physiological saline or distilled water. DMSO was used by direct addition or after dilution with a basal medium, physiological saline or with distilled water. Butyric acid was dissolved in a basal medium, physiological saline or distilled water to prepare a solution containing 1M butyric acid, which was then stored at 4° C. For use, the solution was diluted with a solvent. Hydrocortisone was dissolved in ethanol to prepare a solution containing 40 mM hydrocortisone, which was then stored at 4° C. For use, the solution was diluted with a basal medium. After culturing the number of cells and AE activity were measured.

An AE activity was measured using a synthetic substrate $[^{125}I]$-Ac-Tyr-Phe-Gly (Biochem. Biophys. Res. Commun., Vol. 137, p. 984–991, 1989; and Japanese Unexamined Patent Publication (Kokai) No. 1-104168). One unit of activity is defined as the amount of enzyme that gives 50% conversion of Ac-Tyr-Phe-Gly to Ac-Tyr-Phe-NH$_2$ under standard assay conditions (Biochem. Biophys. Res. Commun. Vol. 137, p. 984–991 (1986)).

In addition, to confirm an effectiveness of TSA in the production of a substance in other cell line, effect of TSA on human interferon-$\gamma$(hIFN-$\gamma$)-producing cells derived from C127I cell line (Proc. Natl. Acad. Sci. USA, Vol. 81, p. 5086–5090, 1984) was tested.

The hIFN-$\gamma$-producing cells were inoculated into 24-well plate with D-MEM (GIBCO) supplemented with 10% CS CHy clone. After incubation at 73° C., for 3 hours so that the cells adhered to the bottom surface of the plate, TSA was added thereon and the cells were cultured. After the culture, the number of cells was counted, and hIFN-$\gamma$ contained in the culture supernatant obtained was quantitated by ELISA as following.

Operation 1: prior to quantitation of hIFN-$\gamma$, 100 $\mu$l/well of a standard solution of hIFN-$\gamma$ (adjusted to 1.0 $\mu$g/ml of hIFN-$\gamma$ concentration by dilution of the stock solution with a coating buffer (0.05M carbonate buffer, pH 9.6)) was added to a 96-well immuno plate (E.I.A/R.I.A. Prate, Coster), and the plate was allowed to stand overnight at 40C. On the next day, the hIFN-$\gamma$ standard solution in the wells was discarded, and the wells were washed with 200 $\mu$l/well of a washing solution comprising Dulbecco's PBS(−) (Nissui Seiyaku) supplemented with 0.1% Tween 20 (BIO-RAD). Note that the washing solution is designated "T-PBS" hereinafter. After removing the T-PBS remaining in the wells, 150 $\mu$l/well of a blocking solution comprising Dulbecco's PBS(−) supplemented with 1.0% gelatin (BIO-RAD) was added to the wells, which were then incubated 37° C. for 2 hours. After the incubation, the blocking solution was discarded from the wells, which were then washed 5 times with T-PBS, and the T-PBS remaining in the wells was removed.

In parallel with the above-mentioned Operation 1, the following operation was carried out.

Operation 2: Standard solutions of hIFN-$\gamma$ (0 to 62.5 ng/ml, $2^n$ stepwise dilutions) diluted with a sample buffer (Dulbecco's PBS(−) containing 0.1% gelatin, 0.1% Tween 20, 0.1% NaN$_3$, 0.05% EGTA (SIGMA) and 0.4 mM MgCl$_2$, dissolved therein) and a sample to be measured (culture supernatant, $2^n$ stepwise dilution) were added to a 96-well V bottom plate (Costar) in an amount of 90 $\mu$l/well. In addition, 90 $\mu$l/well of 20 ng/ml mouse anti-hIFN-$\gamma$ monoclonal antibody diluted with the sample buffer was added thereon, and incubation was carried out at 37° C. for 2 hours. After the incubation the V bottom plate was centrifuged at 4° C. and 1500 rpm for 10 minutes. 100 $\mu$l/well of the supernatant obtained by the Operation 2 was added to the plate treated by the Operation 1, and the plate was incubated at 37° C. for 2 hours. After 5 times washing the plate with the T-PBS, 100 $\mu$l/well of a biotinilated anti-mouse Ig antibody (Amersham) diluted 1000 times with the sample buffer was added to the plate, which was then incubated at 37° C. for one hour. After 5 times washing the plate with T-PBS, 100 μl/ml of alkaline phosphatase-avidine (DAKOPATTS) diluted 1000 times with the sample buffer was added to the plate, which was then incubated at 37° C. for 30 minutes. After 5 times washing the plate with T-PBS, 100 μl/well of pNPPA.2Na solution (substrate solution; prepared by alkaline phosphatase substrate solution kit (BIO-RAD) was added to the plate, which was then incubated at 37° C. for 10 to 20 minutes. At a time point at which coloring reached to an appropriate level, 100 μl/ml of 2N NaOH was added to stop the reaction, and absorbance at 405 nm was measured.

In comparison of TSA, DMSO, butyric acid and hydrocortisone for enhancement of the production of AE, the optimum concentrations were 200 nM, 1% (about 140 nM), 1 mM and 1 μM, respectively, and at these concentrations, amounts of AE per medium were 4.7, 1.9, 3.9 and 1.1 relating to the amount of AE 1.0 produced under the condition of non-addition. From these results, it was shown that TSA is more effective than DMSO, butyric acid and hydrocortisone in enhancement of AE production. An amount of AE increased by DMSO or hydrocortisone is smaller than that by TSA and butyric acid, and therefore one cannot say that DMSO and hydrocortisones are effective for enhancement of AE production. Butyric acid exhibited cell damage at 1 mM or more, while TSA did not exhibit cell-damage at 200 nM at which the strongest enhancement effect of AE production was shown. Moreover, TSA exhibited the strongest enhancement of AE production at a concentration of one five thousandth that of butyric acid.

As can be seen from the above, TSA can effectively increase an amount per medium of a protein produced at a low concentration without cell-damage, and therefore largely contributes to production, especially industrial production of a desired substance.

In addition, in the production of hIFN-γ using C127I cells as a host, TSA is shown to be effective to enhance the productivity. This means that TSA is useful for the enhancement of the productivity of a desired protein regardless the kinds of desired proteins to be produced and the species of cells to be used.

Therefore, according to the present invention, in addition to the proteins shown in Examples, the productivity of any proteins listed above can be enhanced. Particular examples of proteins to which the present process may be applied include interleukin (see, Japanese Unexamined Patent Publication (Kokai) No. 63-185387), peptidyl C-terminal α-amidating enzyme and derivatives thereof (for example, 799DraI, 799RV, 799Sal I, Δ799, 799–457Δ, 799BstE II$^L$; see Japanese Unexamined Patent Publication (Kokai) No. 1-104168; SEQ ID NO: 1), XA (see, Japanese Unexamined Patent Publication (Kokai) No. 1-104168; SEQ ID NO: 2), megakaryocyte differentiation factor (see, Japanese Patent Application No. 5-197752), and the like, which are produced by animal cells transformed with a vector comprising a gene coding for an amino acid sequence of the corresponding protein.

EXAMPLES

Now the present invention is explained in detail by Examples, though the scope of the present invention is not limited to the Examples.

Reference Example 1

Preparation of 3μ-1S cells

Desired 3μ-1S cells were cloned according to a procedure described in Japanese Unexamined Patent Publication (Kokai) No. 2-190193, from MTX 3 μM resistant 9C cell line described in Japanese Unexamined Patent Publication (Kokai) No. 2-190193, obtained from a plasmid encoding the amino acid sequence from −39 to 836 in the amino acid sequence shown in SEQ ID NO: 1. Namely, the MTX 3 μM resistant 9C cells were inoculated to a 96-well plate (Corning), and cultured for one week in 100 μl/well medium comprising nucleic acid-free Minimum Essential Medium (MEM) Alpha Medium (α⁻ MEM, GIBCO) supplemented with 10% dialyzed fetal bovine serum (FBS). In addition, 100 μl/well of a MEM was added thereon, and the cells were cultured for one week. Cells thus obtained having high productivity of the AE were designated 3μ-1 cells. Next, the 3μ-1 cells were suspended by shaking culture (culture volume: 60 ml/flask) in F-12 medium supplemented with 10% FBS and 1.0 μM MTX using a 300 ml conical flask. Next, serum concentration in the medium was gradually decreased, and finally, the cells were adapted to a serum-free medium which was F-12 medium supplemented with 5 μg/ml each of insulin and transferrin and 1.0 μM MTX. In this way, a 3μ-1S cell line, which could grow in suspension with the serum-free medium, was established from the 3μ-1 cell line.

Example 1

Effects of TSA on AE-Producing Cells

The 3μ-1S cells obtained in Reference Example 1, were suspended to a cell density of 4×10⁵ cells/ml in a serum-free medium comprising as a basal medium F-12 medium, supplemented with 5 μg/ml each of insulin and transferrin, and 1 ml/well of the suspension was inoculated into a 24-well culture plate. After the inoculation, 10 μl/well of TSA solution adjusted to 100 times concentration (300 nM to 30 μM) was added to the wells (final concentration; 3 to 300 nM), and the cells were cultured at 37° C. in 5% $CO_2$/air for 3 days. After the culture, the number of cells was counted, and a culture supernatant was recovered by centrifugation (1000 rpm, for 5 minutes). The number of cells was counted by a micro cell counter (Toa Iyo Denshi) or a hemacytometer. An activity of AE contained in the recovered culture supernatant was measured as described above. A result is shown in Table 1.

TABLE 1

| TSA concentration (nM) | Amount of AE produced per medium (U/ml) |
|---|---|
| 0 | 708 |
| 3 | 771 |
| 10 | 866 |
| 20 | 1187 |
| 30 | 1329 |
| 40 | 1077 |
| 50 | 1897 |
| 70 | 1733 |
| 100 | 1894 |
| 150 | 2110 |
| 200 | 3359 |
| 300 | 2829 |

An amount of AE produced increased as an amount of TSA added increased, and the addition of 200 nM TSA provided the maximum productivity, which corresponds to 4.7 times of that provided by non-addition. In addition, inhibition of cell growth was observed depending on a concentration of TSA added, wherein the cell grew to 8.11×10⁵ cells/ml when TSA was not added, while the cells grew to 5.77×10⁵ cells/ml when 200 nM TSA was added.

The latter cell concentration is higher than the cell concentration of the inoculated cells ($4\times10^5$ cells/ml), showing that although the addition of 200 nM TSA inhibited the cell growth but did not damage the cells. When TSA was added to 300 nM concentration, the cell concentration decreased to $3.64\times10^5$ cells/ml, a little of cell-damage was observed.

The above result shows that the order of nM of TSA is effective for enhancement of AE production. Namely, up to 300 nM, or more preferably up to 200 nM TSA is suitable for enhancement of AE production, without cell-damage.

Example 2

Effects of DMSO on AE-Producing Cells

According to the same procedure as described above, effects of DMSO on AE-producing cells were tested by adding a final concentration of 0.01 to 8% DMSO. A result is shown in Table 2.

TABLE 2

| DMSO concentration (%) | Amount of AE produced per medium (U/ml) |
| --- | --- |
| 0 | 753 |
| 0.01 | 828 |
| 0.125 | 859 |
| 0.25 | 786 |
| 0.5 | 1045 |
| 1.0 | 1411 |
| 2.0 | 1354 |
| 4.0 | 200 |
| 8.0 | 50 |

Although the addition of 1% DMSO provided the maximum productivity of AE, the increase of the productivity was as low as 1.9 times of that for non-addition control. In addition, at that concentration, no cell-damage was observed (no-addition of DMSO: $9.65\times10^5$ cells/ml; 1% DMSO: $7.54\times10^5$ cells/ml). The addition of more than 2% DMSO provided remarkable morphological change of cells and the cell-damage, and an amount of AE produced per media severely decreased.

Example 3

Effects of Butyric Acid on AE-Producing Cells

According to the same procedure as described above, effects of butyric acid on AE-producing cells were tested by adding a final concentration of 1 nM to 4 mM butyric acid. A result is shown in Table 3.

TABLE 3

| Butyric acid concentration (mM) | Amount of AE produced per medium (U/ml) |
| --- | --- |
| 0 | 774 |
| $10^{-6}$ | 690 |
| $10^{-5}$ | 741 |
| $10^{-4}$ | 780 |
| $10^{-3}$ | 788 |
| $10^{-2}$ | 800 |
| $10^{-1}$ | 1462 |
| 0.25 | 1032 |
| 0.5 | 2582 |
| 1.0 | 3052 |
| 2.0 | 2325 |
| 4.0 | 1258 |

The addition of 0.1 mM butyric acid began to increase AE productivity and the addition of 1 mM butyric acid provides the maximum production of AE, which was about 3.9 times of that for non-addition control. A concentration of butyric acid, at which TSA enhanced AE production, did not provided enhancement of AE production. A dencity of cells cultured under butyric acid-free condition was $9.56\times10^5$ cells/ml, while a dencity of cells under the addition of 1 mM butyric acid which provided the maximum AE productivity was $3.54\times10^5$ cells/ml which was fewer than the number of inoculated cells, showing cell-damage. At a concentration of more than 1 mM butyric acid added, cell-damage became more conspicuous severer and an AE productivity severely decreased.

Example 4

Effects of Hydrocortisone on AE-Producing Cells

According to the same procedure as described above, effects of hydrocortisone on AE-producing cells were tested by using a final concentration of 100 nM to 1 mM hydrocortisone. A result is shown in Table 4.

TABLE 4

| Hydrocortisone concentration ($\mu$M) | Amount of AE produced per medium (units/ml) |
| --- | --- |
| 0 | 890 |
| 0.1 | 873 |
| 1 | 1002 |
| 10 | 827 |
| 100 | 334 |
| 1000 | 104 |

Although the addition of 1 $\mu$M hydrocortisone provided the maximum AE production, a ratio of increase is as small as 1.1 times comparing to the production of AE under hydrocortisone-free condition. At a concentration of hydrocortisone of more than 10 $\mu$M, AE production remarkably decreased. In addition, the cell growth was inhibited as a concentration of hydrocortisone increased, and the addition of 1 mM hydrocortisone provided cell-damage (no-addition: $10.50\times10^5$ cells/ml; 1 mM: $3.32\times10^5$ cells/ml). As seen from the above, enhancement of AE production by hydrocortisone in AE-producing cells was very low.

Example 5

Effects of TSA on Human Interferon-$\gamma$ (hIFN-$\gamma$) Production in C127I Cells as Host First, hIFN-producing cells obtained by trypsin treatment and centrifugation were suspended in D-MEM medium supplemented with 10% CS, and the suspension was inoculated to a 24-well culture plate at an amount of $2.5\times10^4$ cells/cm$^2$ and 1 ml/well. After incubation at 37° C. for 3 hours so that the cells adhered to the bottom of the plate, TSA was added to the plate to make a final concentration of TSA 0.82 to 200 nM, and the cells were cultured at 37° C. in 5% CO$_2$/air for 3 days. After the culture a culture supernatant was obtained by centrifugation, and the cells were recovered by trypsin treatment, and the number of the cells was counted. In addition, hIFN-$\gamma$ contained in the culture supernatant thus obtained was quantitated by ELISA as described above. A result is shown in Table 5.

TABLE 5

| TSA concentration (nM) | Amount of hIFN-γ produced per medium (ng/ml) |
|---|---|
| 0 | 81.4 |
| 0.82 | 202.2 |
| 2.47 | 215.1 |
| 7.41 | 108.7 |
| 22.2 | 137.8 |
| 66.7 | 58.1 |
| 200 | 59.1 |

An enhancement of production of hIFN-γ was observed at the addition of 0.82 nM (820 μM) TSA (2.5 times of TSA-free condition), reached the maximum level at 2.47 nM TSA, which level was 2.6 times of that of TSA-free condition. At this concentration, no cell growth inhibition and cell-damage were observed (TSA non-addition: $3.94 \times 10^5$ cells/cm$^2$; 2.47 nM; $4.15 \times 10^5$ cells/cm$^2$). Growth inhibition was observed at a concentration of TSA added of more than 7.41 nM. As seen from the above, it was shown that TSA is effective for hIFN-γ production in C127I cells as host. It was shown that the addition of TSA in the order of concentration of μM enhances the productivity of a desired protein, depending on the species of cells used.

According to the present invention, a productivity of a desired protein by culturing a producer animal cells in a medium is enhanced by adding a trichostatin compound to the medium. The enhancement of the productivity in turn may reduce a production cost and shorten the time of culturing. In addition, since a concentration of a desired protein in a medium becomes high, and cells are not damaged, isolation and purification of the desired protein becomes easier. Therefore, the present process is highly advantageous in an industrial production of a desired protein by animal cell culture.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2625 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2625

( i x ) FEATURE:
        ( A ) NAME/KEY: mat_peptide
        ( B ) LOCATION: 118..2625

( x i ) SEQUENCE DESCRIPTION: SEQ ID NO:1:

```
ATG  GAT  ATG  GCC  AGC  CTC  ATT  AGC  AGC  TTG  CTT  GTG  CTC  TTT  CTC  ATA        48
Met  Asp  Met  Ala  Ser  Leu  Ile  Ser  Ser  Leu  Leu  Val  Leu  Phe  Leu  Ile
-39            -35                           -30                          -25

TTT  CAG  AAC  AGC  TGT  TAC  TGT  TTC  AGA  AGT  CCC  CTC  TCT  GTC  TTT  AAG        96
Phe  Gln  Asn  Ser  Cys  Tyr  Cys  Phe  Arg  Ser  Pro  Leu  Ser  Val  Phe  Lys
               -20                      -15                          -10

AGG  TAT  GAG  GAA  TCA  ACC  AGA  TCA  CTT  TCC  AAT  GAC  TGC  TTG  GGA  ACC       144
Arg  Tyr  Glu  Glu  Ser  Thr  Arg  Ser  Leu  Ser  Asn  Asp  Cys  Leu  Gly  Thr
          -5                       -1    1                    5

ACA  CGG  CCC  GTT  ATG  TCT  CCA  GGC  TCA  TCA  GAT  TAT  ACT  TTA  GAT  ATC       192
Thr  Arg  Pro  Val  Met  Ser  Pro  Gly  Ser  Ser  Asp  Tyr  Thr  Leu  Asp  Ile
10                       15                      20                          25

CGA  ATG  CCA  GGA  GTA  ACT  CCG  ACA  GAG  TCG  GAC  ACG  TAT  CTT  TGC  AAG       240
Arg  Met  Pro  Gly  Val  Thr  Pro  Thr  Glu  Ser  Asp  Thr  Tyr  Leu  Cys  Lys
                    30                      35                          40

TCT  TAC  CGG  CTG  CCA  GTG  GAT  GAT  GAA  GCC  TAC  GTA  GTT  GAC  TAC  AGA       288
Ser  Tyr  Arg  Leu  Pro  Val  Asp  Asp  Glu  Ala  Tyr  Val  Val  Asp  Tyr  Arg
               45                       50                          55

CCA  CAT  GCC  AAT  ATG  GAT  ACT  GCA  CAT  CAC  ATG  CTC  CTA  TTT  GGA  TGC       336
Pro  His  Ala  Asn  Met  Asp  Thr  Ala  His  His  Met  Leu  Leu  Phe  Gly  Cys
               60                       65                          70
```

```
AAT  GTG  CCT  TCT  TCC  ACT  GAT  GAT  TAC  TGG  GAC  TGC  AGT  GCA  GGA  ACT        384
Asn  Val  Pro  Ser  Ser  Thr  Asp  Asp  Tyr  Trp  Asp  Cys  Ser  Ala  Gly  Thr
     75                  80                       85

TGT  AAT  GAC  AAA  TCT  AGT  ATA  ATG  TAT  GCC  TGG  GCA  AAG  AAT  GCA  CCA        432
Cys  Asn  Asp  Lys  Ser  Ser  Ile  Met  Tyr  Ala  Trp  Ala  Lys  Asn  Ala  Pro
90                       95                      100                      105

CCC  ACC  AAA  CTA  CCA  GAA  GGA  GTT  GGA  TTT  CAA  GTT  GGA  GGG  AAA  TCG        480
Pro  Thr  Lys  Leu  Pro  Glu  Gly  Val  Gly  Phe  Gln  Val  Gly  Gly  Lys  Ser
                    110                      115                      120

GGC  AGT  AGA  TAT  TTT  GTT  CTT  CAA  GTT  CAC  TAT  GGT  GAT  GTG  AAA  GCA        528
Gly  Ser  Arg  Tyr  Phe  Val  Leu  Gln  Val  His  Tyr  Gly  Asp  Val  Lys  Ala
               125                      130                      135

TTC  CAG  GAT  AAA  CAT  AAA  GAT  TGC  ACA  GGG  GTG  ACT  GTA  CGG  ATA  ACA        576
Phe  Gln  Asp  Lys  His  Lys  Asp  Cys  Thr  Gly  Val  Thr  Val  Arg  Ile  Thr
          140                      145                      150

CCT  GAA  AAA  CAA  CCA  TTA  ATT  GCA  GGC  ATT  TAT  CTT  TCA  ATG  TCT  CTC        624
Pro  Glu  Lys  Gln  Pro  Leu  Ile  Ala  Gly  Ile  Tyr  Leu  Ser  Met  Ser  Leu
     155                      160                      165

AAC  ACT  GTT  GTT  CCA  CCT  GGG  CAA  GAG  GTA  GTT  AAT  TCT  GAT  ATT  GCC        672
Asn  Thr  Val  Val  Pro  Pro  Gly  Gln  Glu  Val  Val  Asn  Ser  Asp  Ile  Ala
170                      175                      180                      185

TGC  CTC  TAC  AAC  AGA  CCA  ACG  ATA  CAC  CCA  TTT  GCC  TAC  AGA  GTC  CAT        720
Cys  Leu  Tyr  Asn  Arg  Pro  Thr  Ile  His  Pro  Phe  Ala  Tyr  Arg  Val  His
               190                      195                      200

ACT  CAT  CAG  TTA  GGG  CAG  GTG  GTG  AGC  GGC  TTT  AGA  GTC  AGA  CAT  GGC        768
Thr  His  Gln  Leu  Gly  Gln  Val  Val  Ser  Gly  Phe  Arg  Val  Arg  His  Gly
          205                      210                      215

AAA  TGG  ACT  TTA  ATT  GGC  AGA  CAA  AGC  CCA  CAG  CTG  CCA  CAG  GCG  TTT        816
Lys  Trp  Thr  Leu  Ile  Gly  Arg  Gln  Ser  Pro  Gln  Leu  Pro  Gln  Ala  Phe
     220                      225                      230

TAC  CCT  GTA  GAG  CAT  CCA  TTA  GAG  ATT  AGC  CCT  GGA  GAT  ATT  ATA  GCA        864
Tyr  Pro  Val  Glu  His  Pro  Leu  Glu  Ile  Ser  Pro  Gly  Asp  Ile  Ile  Ala
235                      240                      245

ACC  AGG  TGT  CTG  TTC  ACT  GGT  AAA  GGA  AGG  ATG  TCG  GCG  ACA  TAT  ATT        912
Thr  Arg  Cys  Leu  Phe  Thr  Gly  Lys  Gly  Arg  Met  Ser  Ala  Thr  Tyr  Ile
250                      255                      260                      265

GGG  GGC  ACA  GCT  AAA  GAT  GAA  ATG  TGT  AAT  TTA  TAC  ATC  ATG  TAT  TAC        960
Gly  Gly  Thr  Ala  Lys  Asp  Glu  Met  Cys  Asn  Leu  Tyr  Ile  Met  Tyr  Tyr
               270                      275                      280

ATG  GAT  GCT  GCC  CAT  GCT  ACT  TCA  TAC  ATG  ACC  TGT  GTA  CAG  ACA  GGT       1008
Met  Asp  Ala  Ala  His  Ala  Thr  Ser  Tyr  Met  Thr  Cys  Val  Gln  Thr  Gly
          285                      290                      295

AAC  CCA  AAG  CTA  TTT  GAA  AAC  ATC  CCT  GAG  ATT  GCA  AAT  GTT  CCG  ATT       1056
Asn  Pro  Lys  Leu  Phe  Glu  Asn  Ile  Pro  Glu  Ile  Ala  Asn  Val  Pro  Ile
     300                      305                      310

CCT  GTA  AGC  CCT  GAC  ATG  ATG  ATG  ATG  ATG  ATG  ATG  GGA  CAT  GGT  CAC       1104
Pro  Val  Ser  Pro  Asp  Met  Met  Met  Met  Met  Met  Met  Gly  His  Gly  His
315                      320                      325

CAC  CAT  ACA  GAA  GCT  GAG  GCT  GAG  ACG  AAT  ACA  GCA  CTT  CAG  CAG  CCT       1152
His  His  Thr  Glu  Ala  Glu  Ala  Glu  Thr  Asn  Thr  Ala  Leu  Gln  Gln  Pro
330                      335                      340                      345

AAA  CGG  GAG  GAG  GAA  GAA  GTA  TTA  AAT  CAG  GAT  GTC  CAT  CTA  GAA  GAA       1200
Lys  Arg  Glu  Glu  Glu  Glu  Val  Leu  Asn  Gln  Asp  Val  His  Leu  Glu  Glu
                    350                      355                      360

GAT  ACA  GAC  TGG  CCG  GGA  GTG  AAC  CTC  AAA  GTG  GGA  CAA  GTG  TCT  GGT       1248
Asp  Thr  Asp  Trp  Pro  Gly  Val  Asn  Leu  Lys  Val  Gly  Gln  Val  Ser  Gly
               365                      370                      375

TTA  GCG  CTG  GAT  CCC  AAG  AAT  AAT  TTG  GTT  ATT  TTC  CAC  AGG  GGG  GAT       1296
Leu  Ala  Leu  Asp  Pro  Lys  Asn  Asn  Leu  Val  Ile  Phe  His  Arg  Gly  Asp
          380                      385                      390
```

```
CAT  GTC  TGG  GAT  GAA  AAC  TCA  TTT  GAT  AGG  AAT  TTT  GTT  TAT  CAA  CAA   1344
His  Val  Trp  Asp  Glu  Asn  Ser  Phe  Asp  Arg  Asn  Phe  Val  Tyr  Gln  Gln
     395                      400                      405

AGA  GGA  ATC  GGA  CCA  ATC  CAG  GAA  AGC  ACC  ATT  CTC  GTT  GTT  GAT  CCG   1392
Arg  Gly  Ile  Gly  Pro  Ile  Gln  Glu  Ser  Thr  Ile  Leu  Val  Val  Asp  Pro
410                 415                      420                           425

AAC  ACT  TCT  AAA  GTC  CTC  AAG  TCA  ACA  GGG  CAG  AAT  TTG  TTT  TTT  TTG   1440
Asn  Thr  Ser  Lys  Val  Leu  Lys  Ser  Thr  Gly  Gln  Asn  Leu  Phe  Phe  Leu
               430                      435                           440

CCC  CAT  GGC  CTG  ACT  ATA  GAC  AGA  GAT  GGG  AAT  TAT  TGG  GTC  ACA  GAT   1488
Pro  His  Gly  Leu  Thr  Ile  Asp  Arg  Asp  Gly  Asn  Tyr  Trp  Val  Thr  Asp
               445                      450                      455

GTA  GCC  CTT  CAT  CAG  GTT  TTC  AAA  GTG  GGA  GCT  GAA  AAA  GAA  ACG  CCG   1536
Val  Ala  Leu  His  Gln  Val  Phe  Lys  Val  Gly  Ala  Glu  Lys  Glu  Thr  Pro
          460                      465                      470

CTG  CTT  GTA  TTA  GGG  AGG  GCA  TTT  CAG  CCT  GGG  AGC  GAT  CGG  AAG  CAT   1584
Leu  Leu  Val  Leu  Gly  Arg  Ala  Phe  Gln  Pro  Gly  Ser  Asp  Arg  Lys  His
     475                      480                      485

TTC  TGT  CAG  CCA  ACT  GAT  GTT  GCA  GTC  GAC  CCC  ATT  ACT  GGC  AAC  TTC   1632
Phe  Cys  Gln  Pro  Thr  Asp  Val  Ala  Val  Asp  Pro  Ile  Thr  Gly  Asn  Phe
490                      495                      500                      505

TTT  GTG  GCG  GAT  GGC  TAC  TGC  AAC  AGT  CGC  ATC  ATG  CAA  TTC  TCA  CCT   1680
Phe  Val  Ala  Asp  Gly  Tyr  Cys  Asn  Ser  Arg  Ile  Met  Gln  Phe  Ser  Pro
                    510                      515                      520

AAT  GGA  ATG  TTC  ATC  ATG  CAG  TGG  GGA  GAA  GAA  ACA  TCC  TCA  AAC  CTC   1728
Asn  Gly  Met  Phe  Ile  Met  Gln  Trp  Gly  Glu  Glu  Thr  Ser  Ser  Asn  Leu
               525                      530                      535

CCC  CGA  CCT  GGT  CAG  TTC  CGC  ATT  CCA  CAC  AGT  CTG  ACC  ATG  ATA  TCT   1776
Pro  Arg  Pro  Gly  Gln  Phe  Arg  Ile  Pro  His  Ser  Leu  Thr  Met  Ile  Ser
          540                      545                      550

GAC  CAA  GGA  CAG  CTG  TGT  GTG  GCC  GAC  AGA  GAG  AAC  GGC  CGG  ATT  CAG   1824
Asp  Gln  Gly  Gln  Leu  Cys  Val  Ala  Asp  Arg  Glu  Asn  Gly  Arg  Ile  Gln
     555                      560                      565

TGC  TTC  CAT  GCT  AAA  ACG  GGG  GAA  TTT  GTA  AAG  CAA  ATC  AAA  CAT  CAG   1872
Cys  Phe  His  Ala  Lys  Thr  Gly  Glu  Phe  Val  Lys  Gln  Ile  Lys  His  Gln
570                      575                      580                      585

GAA  TTT  GGA  AGA  GAG  GTG  TTT  GCT  GTC  TCA  TAT  GCA  CCA  GGT  GGA  GTG   1920
Glu  Phe  Gly  Arg  Glu  Val  Phe  Ala  Val  Ser  Tyr  Ala  Pro  Gly  Gly  Val
                    590                      595                      600

TTG  TAC  GCT  GTT  AAT  GGA  AAG  CCG  TAC  TAT  GGA  GAT  TCC  ACC  CCT  GTA   1968
Leu  Tyr  Ala  Val  Asn  Gly  Lys  Pro  Tyr  Tyr  Gly  Asp  Ser  Thr  Pro  Val
               605                      610                      615

CAA  GGC  TTT  ATG  CTG  AAT  TTC  TCC  AAT  GGG  GAT  ATT  CTA  GAT  ACA  TTC   2016
Gln  Gly  Phe  Met  Leu  Asn  Phe  Ser  Asn  Gly  Asp  Ile  Leu  Asp  Thr  Phe
          620                      625                      630

ATT  CCT  GCT  AGA  AAG  AAT  TTT  GAA  ATG  CCC  CAT  GAT  ATT  GCT  GCA  GGA   2064
Ile  Pro  Ala  Arg  Lys  Asn  Phe  Glu  Met  Pro  His  Asp  Ile  Ala  Ala  Gly
     635                      640                      645

GAT  GAT  GGA  ACG  GTG  TAT  GTT  GGG  GAT  GCA  CAT  GCC  AAC  GCT  GTA  TGG   2112
Asp  Asp  Gly  Thr  Val  Tyr  Val  Gly  Asp  Ala  His  Ala  Asn  Ala  Val  Trp
650                      655                      660                      665

AAG  TTC  TCC  CCT  TCA  AAG  GCA  GAG  CAT  CGA  TCT  GTC  AAA  AAA  GCT  GGA   2160
Lys  Phe  Ser  Pro  Ser  Lys  Ala  Glu  His  Arg  Ser  Val  Lys  Lys  Ala  Gly
                    670                      675                      680

ATA  GAG  GTA  GAA  GAA  ATA  ACA  GAA  ACC  GAG  ATC  TTC  GAG  ACC  CAT  ATG   2208
Ile  Glu  Val  Glu  Glu  Ile  Thr  Glu  Thr  Glu  Ile  Phe  Glu  Thr  His  Met
               685                      690                      695

AGA  AGC  AGA  CCA  AAG  ACC  AAT  GAA  AGT  GTT  GGG  CAG  CAA  ACA  CAG  GAG   2256
Arg  Ser  Arg  Pro  Lys  Thr  Asn  Glu  Ser  Val  Gly  Gln  Gln  Thr  Gln  Glu
          700                      705                      710
```

```
AAA  CCG  AGT  GTT  GTA  CAA  GAA  AGC  AGC  GCC  GGC  GTC  TCT  TTC  GTT  CTC     2304
Lys  Pro  Ser  Val  Val  Gln  Glu  Ser  Ser  Ala  Gly  Val  Ser  Phe  Val  Leu
     715                      720                     725

ATC  ATC  ACT  CTT  CTA  ATC  ATT  CCT  GTT  GTG  GTT  CTC  ATC  GCT  ATT  GCA     2352
Ile  Ile  Thr  Leu  Leu  Ile  Ile  Pro  Val  Val  Val  Leu  Ile  Ala  Ile  Ala
730                      735                     740                         745

ATC  TTC  ATT  CGT  TGG  AGG  AAA  GTT  AGG  ATG  TAT  GGA  GGT  GAC  ATT  GGC     2400
Ile  Phe  Ile  Arg  Trp  Arg  Lys  Val  Arg  Met  Tyr  Gly  Gly  Asp  Ile  Gly
                    750                     755                     760

CAC  AAA  TCA  GAA  TCC  AGT  TCA  GGG  GGC  ATC  TTG  GGA  AAA  CTT  CGA  GGG     2448
His  Lys  Ser  Glu  Ser  Ser  Ser  Gly  Gly  Ile  Leu  Gly  Lys  Leu  Arg  Gly
               765                     770                     775

AAG  GGC  AGT  GGA  GGC  CTT  AAT  CTG  GGA  ACA  TTC  TTT  GCA  ACG  CAT  AAA     2496
Lys  Gly  Ser  Gly  Gly  Leu  Asn  Leu  Gly  Thr  Phe  Phe  Ala  Thr  His  Lys
          780                     785                     790

GGA  TAT  AGT  AGA  AAA  GGC  TTT  GAC  AGG  CTG  AGT  ACA  GAA  GGA  AGC  GAC     2544
Gly  Tyr  Ser  Arg  Lys  Gly  Phe  Asp  Arg  Leu  Ser  Thr  Glu  Gly  Ser  Asp
          795                     800                     805

CAA  GAG  AAA  GAT  GAT  GAT  GAT  GAT  GGC  TCA  GAC  TCT  GAA  GAA  GAG  TAT     2592
Gln  Glu  Lys  Asp  Asp  Asp  Asp  Asp  Gly  Ser  Asp  Ser  Glu  Glu  Glu  Tyr
810                      815                     820                         825

TCT  GCC  CCG  CCT  ATT  CCA  CCA  GTA  TCT  TCC  TCC                              2625
Ser  Ala  Pro  Pro  Ile  Pro  Pro  Val  Ser  Ser  Ser
                    830                     835
```

( 2 ) INFORMATION FOR SEQ ID NO:2:

( i ) SEQUENCE CHARACTERISTICS:
        ( A ) LENGTH: 1203 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1203

( x i ) SEQUENCE DESCRIPTION: SEQ ID NO:2:

```
ATG  GCC  AGC  CTC  AGT  AGC  AGC  TTT  CTT  GTG  CTC  TTT  CTC  TTA  TTT  CAG       48
Met  Ala  Ser  Leu  Ser  Ser  Ser  Phe  Leu  Val  Leu  Phe  Leu  Leu  Phe  Gln
1                        5                       10                          15

AAC  AGC  TGC  TAC  TGT  TTC  AGG  AGT  CCC  CTC  TCT  GTC  TTT  AAC  AGG  TAT       96
Asn  Ser  Cys  Tyr  Cys  Phe  Arg  Ser  Pro  Leu  Ser  Val  Phe  Asn  Arg  Tyr
               20                       25                      30

GAG  GAA  TCT  ACC  AGA  TCA  CTT  TCC  AAT  GAC  TGC  TTG  GGA  ACC  ACG  CGG      144
Glu  Glu  Ser  Thr  Arg  Ser  Leu  Ser  Asn  Asp  Cys  Leu  Gly  Thr  Thr  Arg
          35                      40                      45

CCC  GTT  ATG  TCT  CCA  GGC  TCA  TCA  GAT  TAT  ACT  CTA  GAT  ATC  CGC  ATG      192
Pro  Val  Met  Ser  Pro  Gly  Ser  Ser  Asp  Tyr  Thr  Leu  Asp  Ile  Arg  Met
     50                      55                      60

CCA  GGA  GTA  ACT  CCG  ACA  GAG  TCG  GAC  ACA  TAT  TTG  TGC  AAG  TCT  TAC      240
Pro  Gly  Val  Thr  Pro  Thr  Glu  Ser  Asp  Thr  Tyr  Leu  Cys  Lys  Ser  Tyr
65                       70                      75                          80

CGG  CTG  CCA  GTG  GAT  GAT  GAA  GCC  TAT  GTA  GTT  GAC  TTC  AGA  CCA  CAT      288
Arg  Leu  Pro  Val  Asp  Asp  Glu  Ala  Tyr  Val  Val  Asp  Phe  Arg  Pro  His
               85                       90                      95

GCC  AAT  ATG  GAT  ACT  GCA  CAT  CAC  ATG  CTT  CTA  TTT  GGA  TGC  AAT  ATA      336
Ala  Asn  Met  Asp  Thr  Ala  His  His  Met  Leu  Leu  Phe  Gly  Cys  Asn  Ile
               100                     105                      110

CCT  TCT  TCC  ACT  GAT  GAT  TAC  TGG  GAC  TGT  AGT  GCG  GGA  ACT  TGC  ATG      384
Pro  Ser  Ser  Thr  Asp  Asp  Tyr  Trp  Asp  Cys  Ser  Ala  Gly  Thr  Cys  Met
```

```
                    115                              120                                  125
GAC  AAA  TCC  AGT  ATA  ATG  TAT  GCC  TGG  GCA  AAG  AAT  GCA  CCA  CCC  ACC            432
Asp  Lys  Ser  Ser  Ile  Met  Tyr  Ala  Trp  Ala  Lys  Asn  Ala  Pro  Pro  Thr
     130                      135                      140

AAA  CTT  CCA  GAA  GGA  GTT  GGC  TTT  CGT  GTT  GGA  GGG  AAA  TCA  GGC  AGT            480
Lys  Leu  Pro  Glu  Gly  Val  Gly  Phe  Arg  Val  Gly  Gly  Lys  Ser  Gly  Ser
145                      150                      155                           160

AGA  TAT  TTT  GTG  CTT  CAA  GTT  CAC  TAT  GGA  AAT  GTG  AAA  GCA  TTC  CAG            528
Arg  Tyr  Phe  Val  Leu  Gln  Val  His  Tyr  Gly  Asn  Val  Lys  Ala  Phe  Gln
               165                      170                           175

GAT  AAA  CAT  AAA  GAT  TGC  ACG  GGG  GTG  ACA  GTA  CGA  GTA  ACA  CCT  GAA            576
Asp  Lys  His  Lys  Asp  Cys  Thr  Gly  Val  Thr  Val  Arg  Val  Thr  Pro  Glu
               180                      185                      190

AAA  CAA  CCG  CAA  ATT  GCA  GGC  ATT  TAT  CTT  TCA  ATG  TCT  GTG  GAC  ACT            624
Lys  Gln  Pro  Gln  Ile  Ala  Gly  Ile  Tyr  Leu  Ser  Met  Ser  Val  Asp  Thr
          195                      200                      205

GTT  ATT  CCA  CCT  GGG  GAA  GAG  GCA  GTT  AAT  TCT  GAT  ATC  GCC  TGC  CTC            672
Val  Ile  Pro  Pro  Gly  Glu  Glu  Ala  Val  Asn  Ser  Asp  Ile  Ala  Cys  Leu
          210                      215                      220

TAC  AAC  AGG  CCG  ACA  ATA  CAC  CCA  TTT  GCC  TAC  AGA  GTC  CAC  ACT  CAT            720
Tyr  Asn  Arg  Pro  Thr  Ile  His  Pro  Phe  Ala  Tyr  Arg  Val  His  Thr  His
225                      230                      235                           240

CAG  TTG  GGG  CAG  GTC  GTA  AGT  GGA  TTT  AGA  GTG  AGA  CAT  GGC  AAG  TGG            768
Gln  Leu  Gly  Gln  Val  Val  Ser  Gly  Phe  Arg  Val  Arg  His  Gly  Lys  Trp
               245                      250                           255

TCT  TTA  ATT  GGT  AGA  CAA  AGC  CCA  CAG  CTG  CCA  CAG  GCA  TTT  TAC  CCT            816
Ser  Leu  Ile  Gly  Arg  Gln  Ser  Pro  Gln  Leu  Pro  Gln  Ala  Phe  Tyr  Pro
               260                      265                      270

GTA  GAG  CAT  CCA  GTA  GAG  ATT  AGC  CCT  GGG  GAT  ATT  ATA  GCA  ACC  AGG            864
Val  Glu  His  Pro  Val  Glu  Ile  Ser  Pro  Gly  Asp  Ile  Ile  Ala  Thr  Arg
          275                      280                      285

TGT  CTG  TTC  ACT  GGT  AAA  GGC  AGG  ACG  TCA  GCA  ACA  TAT  ATT  GGT  GGC            912
Cys  Leu  Phe  Thr  Gly  Lys  Gly  Arg  Thr  Ser  Ala  Thr  Tyr  Ile  Gly  Gly
290                      295                      300

ACA  TCT  AAC  GAT  GAA  ATG  TGT  AAT  TTA  TAC  ATC  ATG  TAT  TAC  ATG  GAT            960
Thr  Ser  Asn  Asp  Glu  Met  Cys  Asn  Leu  Tyr  Ile  Met  Tyr  Tyr  Met  Asp
305                      310                      315                           320

GCG  GCC  CAT  GCT  ACG  TCA  TAC  ATG  ACC  TGT  GTA  CAG  ACG  GGT  GAA  CCA           1008
Ala  Ala  His  Ala  Thr  Ser  Tyr  Met  Thr  Cys  Val  Gln  Thr  Gly  Glu  Pro
               325                      330                      335

AAG  TTA  TTT  CAA  AAC  ATC  CCT  GAG  ATT  GCA  AAT  GTT  CCC  ATT  CCT  GTA           1056
Lys  Leu  Phe  Gln  Asn  Ile  Pro  Glu  Ile  Ala  Asn  Val  Pro  Ile  Pro  Val
               340                      345                      350

AGC  CCT  GAC  ATG  ATG  ATG  ATG  ATG  GGA  CAT  GGT  CAC  CAC  CAT  ACA  GAA           1104
Ser  Pro  Asp  Met  Met  Met  Met  Met  Gly  His  Gly  His  His  His  Thr  Glu
          355                      360                      365

GCT  GAG  CCT  GAG  AAG  AAT  ACA  GGA  CTT  CAG  CAG  CCT  AAA  CGG  GAG  GAG           1152
Ala  Glu  Pro  Glu  Lys  Asn  Thr  Gly  Leu  Gln  Gln  Pro  Lys  Arg  Glu  Glu
          370                      375                      380

GAA  GAA  GTA  TTA  GAT  CAG  GGT  CTC  ATT  ACC  TTA  GGG  GAT  AGC  GCA  GTG           1200
Glu  Glu  Val  Leu  Asp  Gln  Gly  Leu  Ile  Thr  Leu  Gly  Asp  Ser  Ala  Val
385                      390                      395                           400

TGA                                                                                      1203
 *
```

We claim:

1. A process for enhancing the production of a protein comprising the steps of:
   (1) culturing animal cells capable of producing the protein in a medium containing trichostatin A; and
   (2) recovering the protein from the culture.

2. A process according to claim 1 wherein the concentration of trichostatin A is between 1 nM and 500 nM.

3. A process according to claim 3, wherein the concentration of trichostatin A is between 20 nM and 300 nM.

4. A process according to claim 3, wherein the concentration of trichostatin A is between 50 nM and 300 nM.

5. A process according to claim 1, wherein the protein is an enzyme.

6. A process according to claim 5, wherein the enzyme is peptidyl C-terminal α-amidating enzyme.

7. A process according to claim 1, wherein the protein is an interferon.

8. A process according to claim 7, wherein the interferon is human interferon-γ.

9. A process according to claim 1, wherein the protein is an interleukin.

10. A process according to claim 9, wherein the interleukin is human interleukin 5.

11. A process according to claim 1, wherein the protein is a growth factor.

12. A process according to claim 1, wherein the protein is a peptide hormone.

13. A process according to claim 1, wherein the protein is a proteinaceous hormone.

14. A process according to claim 1, wherein the animal cells are CHO cells.

15. A process according to claim 14, wherein the protein is an interleukin or an enzyme.

16. A process according to claim 15, wherein the interleukin is human interleukin-5.

17. A process according to claim 15, wherein the enzyme is peptidyl C-terminal α-amidating enzyme.

18. A process according to claim 1, wherein the animal cells are C1271 cells.

19. A process according to claim 18, wherein the protein is an interferon.

20. A process according to claim 19, wherein the interferon is human interferon-γ.

* * * * *